(12) United States Patent
Ryan

(10) Patent No.: US 6,572,659 B1
(45) Date of Patent: Jun. 3, 2003

(54) PROSTHETIC FOOT

(76) Inventor: Michael W. Ryan, 6239 Cypress Ave., El Cerrito, CA (US) 94530

( * ) Notice: Subject to any disclaimer, the term of this patent is extended or adjusted under 35 U.S.C. 154(b) by 4 days.

(21) Appl. No.: 10/004,204

(22) Filed: Nov. 1, 2001

(51) Int. Cl.[7] .................................................. A61F 2/66
(52) U.S. Cl. ......................................... 623/55; 623/52
(58) Field of Search ..................................... 623/47–56

(56) References Cited

U.S. PATENT DOCUMENTS

| | | |
|---|---|---|
| 3,754,286 A | 8/1973 | Ryan |
| 5,376,140 A | 12/1994 | Ryan |

Primary Examiner—David H. Willse
(74) Attorney, Agent, or Firm—Jack Lo

(57) ABSTRACT

A prosthetic foot is comprised of a springy internal frame embedded in a resilient foot-shaped outer body. The frame is in the shape of a modified trapezoid, wherein the shorter top member and the longer bottom member are connected by a generally vertical back member, and a substantially oblique front member. A toe member extends from the bottom member into a toe portion of the outer body. A solid carbon fiber layer is embedded in the frame for strength and elasticity. A break is provided between the lower end of the front member and the bottom member to enable the toe portion of the foot to flex laterally. A flexible cord is connected across the break to prevent the front and bottom portions of the frame from separating when the foot kicks an obstacle.

14 Claims, 3 Drawing Sheets

PROSTHETIC FOOT

BACKGROUND OF THE INVENTION

1. Field of the Invention

This invention relates generally to prosthetic feet.

2. Prior Art

A footstep is comprised of a downward portion when the heel touches the ground, a rocking portion when the foot rocks from back to front on the ground, and a upward portion when the toes lift off the ground. A prosthetic foot mimics the way a real foot absorbs energy on the downward portion of the step to soften the impact, and returns the energy on the upward portion of the step to help the user move forward. These effects are typically achieved by using elastic polymer materials, particularly in the heel and toe portions, to provide longitudinal flexion. However, some prosthetic feet require precision metal components that raise the cost of the feet. The metal parts also tend to wear out and separate from the surrounding plastic parts after a relatively short time. Most importantly, many prosthetic feet lack torsional compliance, that is, they cannot twist about a longitudinal axis. Although they perform well on flat and level surfaces, they lack the necessary torsional compliance when the user steps on an uneven surface, or when the user takes a step with the leg off to a side, such as when playing sports, dancing, etc.

My prior U.S. Pat. No. 5,376,240 discloses a prosthetic foot that provides the important torsional compliance. It is comprised of a internal frame embedded in a foam foot-shaped outer body. The frame is embedded with loose carbon fiber strands for improved strength and elasticity. The frame is in the shape of a modified trapezoid, wherein the back member is generally vertical and the front member is substantially oblique. The lower end of the front member is disconnected from the bottom member, and a bearing is provided at the interface there between. The bearing is comprised of a truncated cone at one mating surface, and a socket at the other mating surface.

The bearing enables the toe part of the foot to twist about the longitudinal axis for compliance on uneven surfaces and when the leg is at an oblique side angle to the ground. However, the loose carbon fiber strands do not provide sufficient strength or elasticity. The rounded heel is not compliant enough to absorb much energy. A short toe member at the front end of the frame terminates before the toe portion of the outer body, so that it does not support the weaker foam toes during the rocking portion of the step. The foam toes do not return much energy, and tend to break very quickly from the repeated bending. Most importantly, the truncated cone separates from the socket when the foot kicks an obstacle, such as a curb, and the foam outer body may tear and cause the user to fall.

OBJECTS OF THE INVENTION

The objects of the present prosthetic foot are:

to have heel and toe portions flex longitudinally on the downward, rocking, and upward portions of a step;

to absorb more energy on the downward portion of the step;

to return more energy on the upward portion of the step;

to be stronger and more elastic;

to have a toe portion with torsional compliance for situations other than walking on a flat surface;

to resist breaking when kicking an obstacle; and to be inexpensive and durable.

Further objects of the present invention will become apparent from a consideration of the drawings and ensuing description.

BRIEF SUMMARY OF THE INVENTION

A prosthetic foot is comprised of a springy internal frame embedded in a resilient foot-shaped outer body. The frame is in the shape of a modified trapezoid, wherein the shorter top member and the longer bottom member are connected by a generally vertical back member, and a substantially oblique front member. A toe member extends from the bottom member into a toe portion of the outer body. A solid carbon fiber layer is embedded in the frame for strength and elasticity. A break is provided between the lower end of the front member and the bottom member to enable the toe portion of the foot to twist about a longitudinal axis. A flexible cord is connected across the break to prevent the front and bottom portions of the frame from separating when the foot kicks an obstacle.

Figure 1:
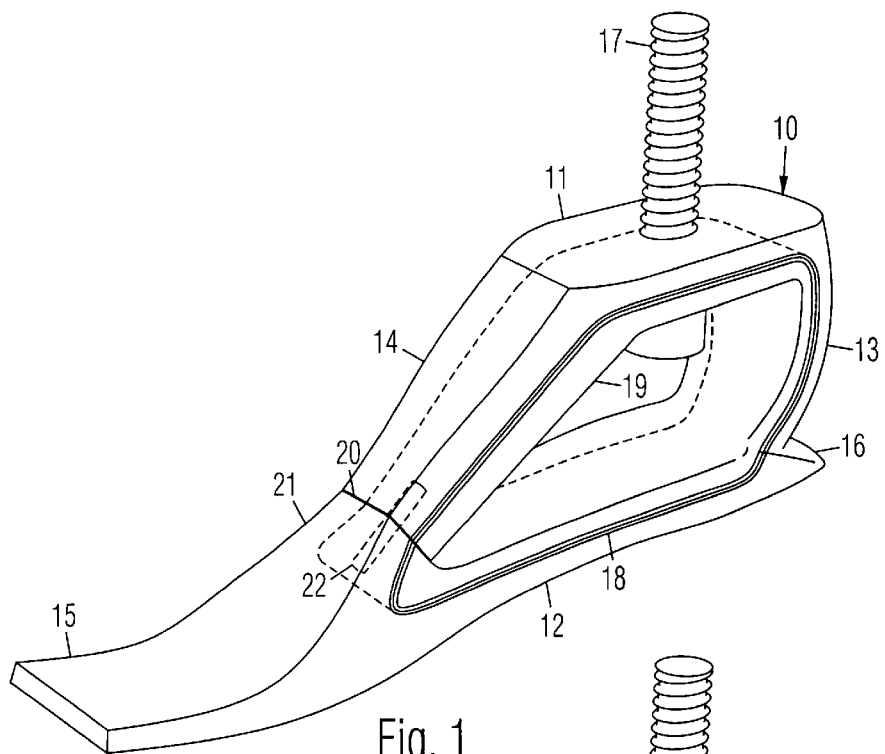
FIG. 1 is a side perspective view of an internal frame of the present prosthetic foot.

| DRAWING REFERENCE NUMERALS | |
| --- | --- |
| 10. Frame | 11. Top Member |
| 12. Bottom Member | 13. Back Member |
| 14. Front Member | 15. Toe Member |
| 16. Heel Extension | 17. Bolt |
| 18. Solid Carbon Fiber Layer | 19. Opening |
| 20. Break | 21. Upturned End |
| 22. Flexible Cord | 23. Outer Body |
| 24. Toe Portion | 25. Reel Portion |

DETAILED DESCRIPTION OF THE INVENTION

FIG. 1:

As shown in FIG. 1, a preferred embodiment of the present prosthetic foot is comprised of a springy internal frame 10. Frame 10 is in the shape of a modified trapezoid, wherein a shorter horizontal top member 11 and a longer horizontal bottom member 12 are connected by a generally vertical back member 13, and a substantially oblique front member 14. Back member 13 is bowed or curved outwardly for shock absorption. A toe member 15 projects forwardly from the front end of bottom member 12. A tapered heel extension 16 projects backwardly from the rear end of bottom member 12. A mounting bolt 17 extends upwardly from top member 11 for attaching to a prosthetic leg. All the members of frame 10 are preferably integrally formed of a strong and springy polymer material, such as a thermoplastic polyester elastomer with a durometer hardness of about 40 D to 72 D for strength and durability.

A solid carbon fiber layer 18 is embedded in frame 10 for additional strength and elasticity. Carbon fiber layer encircles an opening 19 in frame 10 bounded by top member 11, bottom member 12, back member 13, and front member 14. Carbon fiber layer 18 is solid in that it is devoid of polymer material between its fibers.

A break 20 is provided between a lower end of front member 14 and an upturned front end 21 of bottom member 12 to enable torsional compliance in toe portion 15. Break 20 is preferably planar, and is generally orthogonal to front member 14. A flexible cord 22 is connected across break 20 to prevent the lower end of front member 14 from moving laterally or vertically relative to upturned front end 21 of bottom member 12, but enable toe member 15 to twist about a generally longitudinal axis. Further, cord 22 prevents front member 14 and bottom member 12 from separating when the foot kicks an obstacle. Cord 22 is preferably made of "KEVLAR", a synthetic fiber which is several times stronger than steel, so that it can withstand repeated twisting over many years without deteriorating. The lack of precision machined parts in the foot makes it inexpensive to produce.

Figure 2:
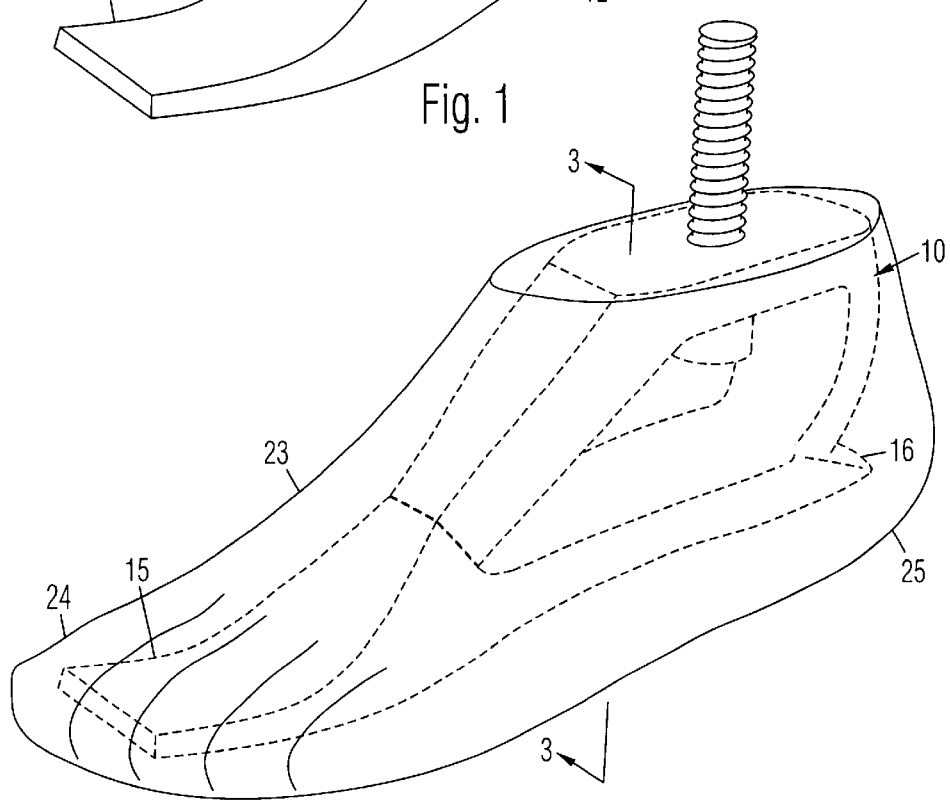
FIG. 2 is a side perspective view of an outer body of the foot.

FIG. 2:

Frame 10 is shown in FIG. 2 embedded in a resilient foot-shaped outer body 23. Only a left foot is shown; a right foot may simply be a mirror image. Outer body 23 is preferably made of a resilient expanded polymer material, such as polyurethane foam. Toe member 15 is fully positioned in a toe portion 24 of outer body 23. Heel extension 16 is positioned in a heel portion 25 of outer body 23.

Figure 3:
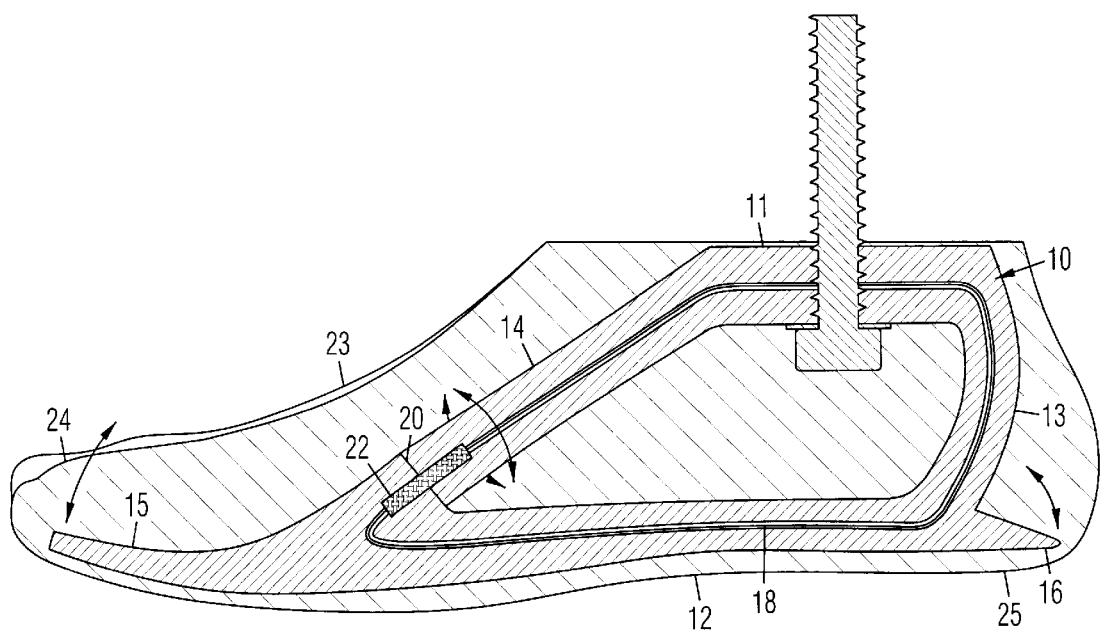
FIG. 3 is a side sectional view of the foot.

FIG. 3:

The prosthetic foot is shown in a sectional view in FIG. 3. Heel extension 16 is positioned in heel portion 25 of outer body 23 for absorbing energy on the downward portion of a step, and for returning energy on the transition from the downward portion to the rocking portion of the step. Toe member 15 is positioned fully in toe portion 24 of outer body 23 for providing torsional compliance and support to the weaker toe portion 24 of outer body 23 at the end of the rocking portion of the step. Cord 22 prevents the lower end of front portion 14 of frame 10 from moving laterally or vertically relative to bottom member 12, and also prevents it from separating from bottom member 12, but allows toe member 15 to twist about a generally longitudinal axis. Frame 10 is preferably molded in polymer, and cord 22 is preferably cast in place during the molding of frame 10 to closely bond the polymer with the fibers in cord 22 for durability. Cord 22 prevents the lower end of front member 14 and bottom member 12 from separating when the foot kicks an obstacle.

Figure 4:
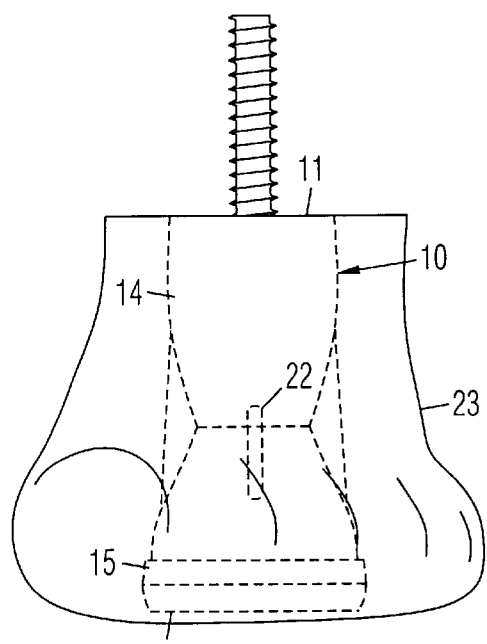
FIG. 4 is a front view of the foot when in a neutral position.
Figure 5:
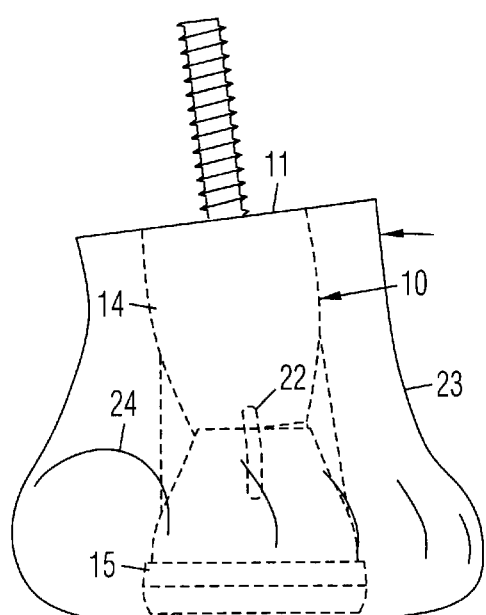
FIG. 5 is a front view of the foot when flexing laterally to the right.
Figure 6:
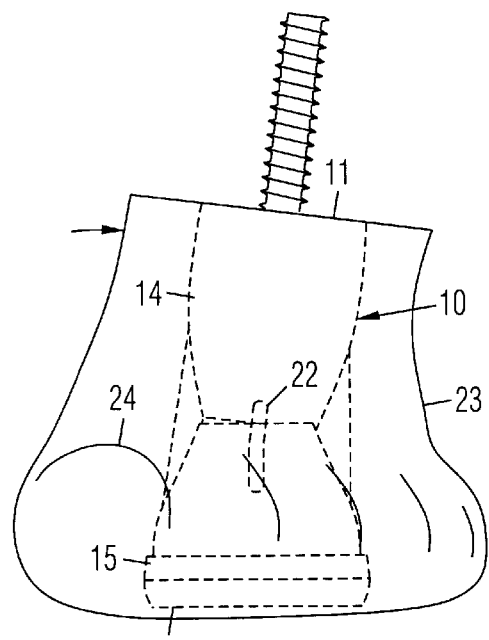
FIG. 6 is a front view of the foot when flexing laterally to the left.

FIGS. 4–6:

The prosthetic foot is shown in a front view in FIG. 4 in a neutral position. Since front member 14 is rotatable about cord 22, top member 11 and toe member 15 are flexible laterally relative to each other, as shown in FIGS. 5 and 6. The twisting in toe member 15 is mostly resisted by the torsional resilience of bottom member 12, but is enough for providing torsional compliance when stepping on an uneven surface, when playing sports, dancing, etc.

Although the foregoing description is specific, it should not be considered as a limitation on the scope of the invention, but only as an example of the preferred embodiment. Many variations are possible within the teachings of the invention. For example, different attachment methods, fasteners, materials, dimensions, etc. can be used unless specifically indicated otherwise. The relative positions of the elements can vary, and the shapes of the elements can vary. Therefore, the scope of the invention should be determined by the appended claims and their legal equivalents, not by the examples given.

I claim:

1. A prosthetic foot, comprising:

a springy frame comprised of a top member and a bottom member connected by a back member and an oblique front member, said bottom member has an upturned front end;

a toe member projecting forwardly from said upturned front end of said bottom member;

a break between a lower end of said front member and said upturned front end of said bottom member to provide torsional compliance in said toe member; and a flexible cord connected across said break to prevent said lower end of said front member from moving laterally and from moving vertically relative to said upturned front end of said bottom member, but enable said toe member to twist about a generally longitudinal axis for torsional compliance, said cord also prevents said front member and said bottom member from separating when said prosthetic foot kicks an obstacle.

2. The prosthetic foot of claim 1, wherein said cord is made of "KEVLAR" for strength and durability.

3. The prosthetic foot of claim 1, wherein said break is generally planar and generally orthogonal to said front member for facilitating rotation.

4. The prosthetic foot of claim 1, further including a springy heel extension projecting backwardly from a rear end of said bottom member.

5. A prosthetic foot, comprising:

a resilient foot-shaped outer body;

a springy internal frame embedded in said outer body, wherein said frame is comprised of a top member and a bottom member connected by a back member and an oblique front member, said bottom member has an upturned front end;

a toe member projecting forwardly from said upturned front end of said bottom member, wherein said toe member is fully positioned in a toe portion of said outer body to support said toe portion;

a break between a lower end of said front member and said upturned front end of said bottom member to provide torsional compliance in said toe member; and a flexible cord connected across said break to prevent said lower end of said front member from moving laterally and from moving vertically relative to said upturned front end of said bottom member, but enable said toe member to twist about a generally longitudinal axis for torsional compliance, said cord also prevents said front member and said bottom member from separating when said prosthetic foot kicks an obstacle.

6. The prosthetic foot of claim 5, wherein said cord is made of "KEVLAR" for strength and durability.

7. The prosthetic foot of claim 5, wherein said break is generally planar and generally orthogonal to said front member for facilitating rotation.

8. The prosthetic foot of claim 5, further including a springy heel extension projecting backwardly from a rear end of said bottom member, wherein said heel extension is positioned in a heel portion of said outer body for absorbing energy.

9. A prosthetic foot, comprising:

a resilient foot-shaped outer body;

a springy internal frame embedded in said outer body, wherein said frame is comprised of a top member and a bottom member connected by a back member and an oblique front member, said bottom member has an upturned front end;

a toe member projecting forwardly from said upturned front end of said bottom member, wherein said toe member is fully positioned in a toe portion of said outer body to support said toe portion;

a solid carbon fiber layer embedded in said frame for additional strength and elasticity, wherein said carbon fiber layer encircles an opening in said frame bounded by said top member, said bottom member, said back member, and said front member;

a break between a lower end of said front member and said upturned front end of said bottom member to provide torsional compliance in said toe member; and a flexible cord connected across said break to prevent said lower end of said front member from moving laterally and from moving vertically relative to said upturned front end of said bottom member, but enable said toe member to twist about a generally longitudinal axis for torsional compliance, said cord also prevents said front member and said bottom member from separating when said prosthetic foot kicks an obstacle.

10. The prosthetic foot of claim 9, wherein said top member, said bottom member, said back member, and said front member of said frame are integrally formed of a thermoplastic polyester elastomer with a durometer hardness of about 40 D to 72 D for strength and durability.

11. The prosthetic foot of claim 9, wherein said outer body is made of a resilient polyurethane foam.

12. The prosthetic foot of claim 9, wherein said cord is made of "KEVLAR" for strength and durability.

13. The prosthetic foot of claim 9, wherein said break is generally planar and generally orthogonal to said front member for facilitating rotation.

14. The prosthetic foot of claim 9, further including a springy heel extension projecting backwardly from a rear end of said bottom member, wherein said heel extension is positioned in a heel portion of said outer body for absorbing energy.

* * * * *